United States Patent [19]

Lombardino

[11] 4,434,164
[45] Feb. 28, 1984

[54] CRYSTALLINE BENZOTHIAZINE DIOXIDE SALTS

[75] Inventor: Joseph G. Lombardino, Niantic, Conn.

[73] Assignee: Pfizer Inc., New York, N.Y.

[21] Appl. No.: 367,067

[22] Filed: Apr. 13, 1982

Related U.S. Application Data

[63] Continuation-in-part of Ser. No. 268,980, Jun. 1, 1981, abandoned.

[51] Int. Cl.³ .................... C07D 401/12; A61K 31/54
[52] U.S. Cl. ...................................... 424/246; 544/49
[58] Field of Search ........................... 544/49; 424/246

[56] References Cited

U.S. PATENT DOCUMENTS

| | | | |
|---|---|---|---|
| 3,591,584 | 7/1971 | Lombardino | 260/243 |
| 4,116,964 | 9/1978 | Zinnes et al. | 544/49 |
| 4,233,299 | 11/1980 | Trummlitz et al. | 424/246 |
| 4,289,879 | 9/1981 | Lombardino | 544/49 |

FOREIGN PATENT DOCUMENTS 1544359  4/1979  United Kingdom .

OTHER PUBLICATIONS

J. G. Lombardino et al., "Potent Antiinflammatory N-Heterocyclic 3-Carboxamides of 4-Hydroxy-2-methyl-2H-1,2-benzothiazine 1,1-Dioxide", *Journal of Medicinal Chemistry*, vol. 16, No. 5, p. 493 (1973).

E. Nelson, "Solution Rate of Theophylline Salts and Effects from Oral Administration", *Journal of the American Pharmaceutical Association*, vol. 46, No. 10, p. 607 (1957).

A. E. Vivino, "Blood Theophylline Concentration Following the Oral Administration of Theophylline Ethylenediamine and Theophylline Isopropanolamine", *Journal of the American Pharmaceutical Association*, vol. 43, p. 234 (1954).

*Primary Examiner*—John M. Ford
*Attorney, Agent, or Firm*—Charles J. Knuth; Peter C. Richardson

[57] ABSTRACT

The water-soluble ethylenediamine, monoethanolamine and diethanolamine salts of N-(2-pyridyl)-2-methyl-4-hydroxy-2H-1,2-benzothiazine-3-carboxamide 1,1-dioxide have been prepared. These novel crystalline salts are useful in therapy as non-steroidal anti-arthritic agents. Methods for preparing these salts from the corresponding acidic starting material and the appropriate amine base are provided.

8 Claims, No Drawings

CRYSTALLINE BENZOTHIAZINE DIOXIDE SALTS

CROSS REFERENCE TO RELATED APPLICATION

This application is a continuation-in-part of co-pending application Ser. No. 268,980, filed June 1, 1981 and now abandoned.

BACKGROUND OF THE INVENTION

This invention relates to new and useful benzothiazine dioxide salts. More particularly, it is concerned with certain novel crystalline, non-hygroscopic, water-soluble salts of N-(2-pyridyl)-2-methyl-4-hydroxy-2H-1,2-benzothiazine-3-carboxamide 1,1-dioxide, which are of especial value in view of their unique combination of chemotherapeutic and physical properties.

In the past, various attempts have been made to obtain new and better anti-inflammatory agents. For the most part, these efforts have involved the synthesis and testing of various steroidal compounds such as the corticosteroids or non-steroidal substances of an acidic nature such as phenylbutazone, indomethacin and the like, including a new agent known as piroxicam. The latter substance is a member of a class of anti-inflammatory 4-hydroxy-2H-1,2-benzothiazine-3-carboxamide 1,1-dioxides described and claimed in U.S. Pat. No. 3,591,584. However, in the continuing search for improved anti-inflammatory agents, there is a definite need for anti-arthritic agents having high water-solubility and other desirable properties and especially adapted for oral, topical or parenteral administration.

SUMMARY OF THE INVENTION

In accordance with the present invention, it has now been found that certain novel crystalline, non-hygroscopic, water-soluble base salts of N-(2-pyridyl)-2-methyl-4-hydroxy-2H-1,2-benzothiazine-3-carboxamide 1,1-dioxide are useful as non-steroidal therapeutic agents for alleviating painful inflammatory conditions such as those caused by rheumatoid arthritis, for example. The novel salts of this invention are selected from the group consisting of the ethylenediamine, monoethanolamine and diethanolamine salts of N-(2-pyridyl)-2-methyl-4-hydroxy-2H-1,2-benzothiazine-3-carboxamide 1,1-dioxide, which is an acidic compound of the formula:

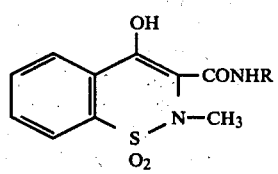

wherein R is 2-pyridyl. The novel ethylenediamine, monoethanolamine and diethanolamine salts of this invention are crystalline, non-hygroscopic, rapidly-dissolving solids with high water solubility and in addition, possess excellent chemical and physical stability properties. Accordingly, they are particularly valuable as non-steroidal therapeutic agents for the treatment of painful inflammatory conditions, especially those caused by rheumatoid arthritis, and are particularly adapted for use in various pharmaceutical dosage forms, including those designed for oral, topical or parenteral administration. The monoethanolamine salt is the preferred salt of this invention.

DETAILED DESCRIPTION OF THE INVENTION

In accordance with the process employed for preparing the novel salts of this invention, N-(2-pyridyl)-2-methyl-4-hydroxy-2H-1,2-benzothiazine-3-carboxamide 1,1-dioxide is contacted with at least an equivalent amount in moles of an organic amine base selected from the group consisting of ethylenediamine, monoethanolamine and diethanolamine. This reaction is normally carried out in a polar protic solvent like water or a lower alkanol such as methanol, ethanol or isopropanol, etc., or in a halogenated hydrocarbon solvent like methylene chloride, chloroform, carbon tetrachloride, ethylene dichloride and s-tetrachloroethane, etc. In general, the reaction is conducted at a temperature that is in the range of from about 20° C. up to about 100° C. for a period of about one-half to about 30 minutes. Upon completion of the reaction, the desired salt product is easily isolated in a conventional manner, e.g., by first evaporating the solvent from the reaction mixture, followed by trituration of the resulting solid residue or crude concentrate product with a suitable solvent system such as ethyl acetate/chloroform, etc. Alternatively, it is also possible to avoid the need for isolation by employing aqueous solutions of the salt as formed in situ by appropriate adjustment in concentration of the solution.

The starting materials required for preparing the novel salts of this invention are all known compounds. For instance, N-(2-pyridyl)-2-methyl-4-hydroxy-2H-1,2-benzothiazine-3-carboxamide 1,1-dioxide (piroxicam) is described in U.S. Pat. No. 3,591,584 to J. G. Lombardino, as well as in the paper of J. G. Lombardino et al., appearing in the *Journal of Medicinal Chemistry*, Vol. 16, p. 493 (1973), including its overall synthesis from readily available organic materials. The amine bases employed to prepare the novel amine addition salts of this invention are all commercially available materials.

The N-(2-pyridyl)-2-methyl-4-hydroxy-2H-1,2-benzothiazine-3-carboxamide 1,1-dioxide salts of the present invention are readily adapted to therapeutic use as anti-arthritic agents. For instance, the monoethanolamine salt of N-(2-pyridyl)-2-methyl-4-hydroxy-2H-1,2-benzothiazine-3-carboxamide 1,1-dioxide, a typical and preferred agent of the present invention, exhibits anti-inflammatory activity in the standard carrageenin-induced rat food edema test [described by C. A. Winter et al., *Proc. Soc. Exp. Biol. Med.*, Vol. 111, p. 544 (1962)], where it was found to cause a substantial inhibition in swelling at the 33 mg/kg dose level when given by the oral route. The herein described benzothiazine dioxide salts exhibit additional advantages. For instance, even though N-(2-pyridyl)-2-methyl-4-hydroxy-2H-1,2-benzothiazine-3-carboxamide 1,1-dioxide (piroxicam) per se is very poorly water-soluble, the monoethanolamine salt of N-(2-pyridyl)-2-methyl-4-hydroxy-2H-1,2-benzothiazine-3-carboxamide 1,1-dioxide is readily flash soluble (i.e., instantaneously soluble) in said solvent and therefore is more rapidly absorbed into the blood stream upon oral administration than the corresponding less soluble calcium salt or even the anhydrous sodium salt of said particular drug (both of which are prepared according to the procedure already set forth in U.S. Pat. No. 3,591,584). Additionally, this particular salt affords a water-clear, conveniently formulated, stable aqueous solution even at very high concentration levels (>100 mg./ml.). The other salts of this invention also afford similar results. This is a truly surprising fact when one considers that the tromethamine salt of N-(2-pyridyl)-2-methyl-4-hydroxy-2H-1,2-benzothiazine-3-carboxamide 1,1-dioxide and the corresponding triethanolamine salt are both poorly water-soluble and that the simple ammonium salt is found to be highly unstable when subjected to drying conditions under vacuum. Moreover, the novel salts of this invention are crystalline, non-hygroscopic, solids which are, accordingly, readily isolated in highly pure form. These particular properties further facilitate the bulk processing of said salts into finished pharmaceutical dosage forms that are especially adapted for use in either oral, topical or parenteral administration, etc.

The herein described salts can be administered as anti-arthritic agents by either of the routes previously indicated. In general, these salts will be administered in doses ranging from about 5.0 mg. up to about 1000 mg. per day, although variations will necessarily occur depending upon the weight and condition of the subject being treated and the particular route of administration chosen. A dosage level that is in the range of from about 0.08 mg. to about 16 mg. per kg of body weight per day is usually preferred, although variations may occur depending upon the individual response to said medicament, as well as on the type of pharmaceutical formulation and the time intervals at which such administration is carried out. In some instances, dosage levels below the lower limit of the aforesaid range may be adequate, while in other cases higher levels may be employed, divided into several smaller doses for administration throughout the day.

The salts of this invention may be administered alone or in combination with pharmaceutically acceptable carriers by the various routes previously indicated, in a wide variety of dosage forms, i.e., they may be combined with various pharmaceutically acceptable inert carriers in the form of tablets, capsules, soft and hard lozenges, troches, hard candies, powders, sprays, creams, salves, suppositories, jellies, pastes, lotions, ointments, aqueous solutions and suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the salts of this invention are present in such dosage forms at concentration levels ranging from about 0.5% to about 90% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in hard geletin capsules; preferred materials also include lactose or milk sugar as well as high molecular weight polyethylene glycols. When aqueous solutions and suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of these amine salts in sesame or peanut oil or in aqueous propylene glycol or aqueous ethanol may be employed, as well as sterile aqueous solutions in distilled water. The aqueous solutions should be suitably buffered (pH>8) and the liquid diluent first rendered isotonic. These aqueous solutions are suitable for intravenous injection purposes. The oily solutions are suitable for intraarticular, intramuscular and subcutaneous injection purposes. Additionally, it is also possible to administer the aforesaid amine addition salts topically when treating inflammatory conditions of the skin or eye by way of creams, jellies, pastes, ointments, solutions and the like, in accordance with standard pharmaceutical practice.

The anti-inflammatory activity of the compounds of the present invention is demonstrated in the previously mentioned standard carrageenin-induced rat foot edema test. In this test, anti-inflammatory activity is determined as the percent inhibition of edema formation in the hind paw of male albino rats (weighing 150–190 g) in response to a sub-plantar injection of carrageenin. The carrageenin is injected as a 1% aqueous suspension (0.05 ml.) one hour after oral administration of the drug, which is normally given in the form of an aqueous solution. Edema formation is then assessed by measuring the volume of the injected paw initially as well as three hours after the carrageenin injection. The increase in volume three hours after carrageenin injection constitutes the individual response. Compounds are considered active if the difference in response between the drug-treated animals (six rats/group) and a control group receiving the vehicle alone is significant on comparison with the results afforded by standard compounds like acetylsalicyclic acid at 100 mg./kg. or phenylbutazone at 33 mg/kg., both by the oral route of administration.

EXAMPLE 1

In a 250 ml. Erlenmeyer reaction flask equipped with a magnetic stirrer, there was placed 500 mg. (0.0015 mole) of N-(2-pyridyl)-2-methyl-4-hydroxy-2H-1,2-benzothiazine-3-carboxamide 1,1-dioxide and 75 ml. of water. Stirring was initiated and to the resulting suspension, there was slowly added 180 mg. (0.003 mole) of ethylenediamine (0.2 ml.). The reaction mixture so obtained was then heated on a steam bath for a period of approximately three minutes to form a yellow solution. Evaporation of the latter solution to near dryness while under reduced pressure then gave a yellow gum, which was subsequently triturated with 200 ml. of chloroform and 30 ml. of ethyl acetate by stirring the mixture for a period of one hour. The resulting pale yellow solid was then recovered by means of suction filtration and washed on the filter funnel with fresh ethyl acetate. In this way, there was ultimately obtained the pure ethylenediamine salt of N-(2-pyridyl)-2-methyl-4-hydroxy-2H-1,2-benzothiazine-3-carboxamide 1,1-dioxide, m.p. 151–154° C. The pure product was further characterized by means of infrared absorption spectra and elemental analysis.

Anal. Calcd. for $C_{15}H_{13}N_3O_4S \cdot C_2H_8N_2$: C, 52.16; H, 5.40; N, 17.89. Found: C, 51.81; H, 5.41; N, 17.77.

EXAMPLE 2

To a suspension of 2.0 g. (0.00604 mole) of N-(2-pyridyl)-2-methyl-4-hydroxy-2H-1,2-benzothiazine-3-carboxamide 1,1-dioxide in 300 ml. of water, there was added 388 mg. (0.00634 mole) of 2-aminoethanol (0.383 ml.) and the resulting mixture was heated on a steam bath for a period of approximately three minutes. The yellow solution so obtained was then filtered to remove a very small amount of water insolubles, followed by concentration of the resulting filtrate in vacuo to yield a yellow oil as the residual liquid. Trituration of the latter material with 200 ml. of an ethyl acetate/chloroform (3:2 by volume) solvent system, followed by stirring at room temperature ($\sim$25° C.) overnight ($\sim$16 hours) under a dry nitrogen atmosphere then gave a solid precipitate which was subsequently recovered by means of suction filtration. After washing the recovered solid material well with ethyl acetate and drying in vacuo to constant weight, there was ultimately obtained a 2.07 g.(87%) yield of the pure monoethanolamine salt of N-(2-pyridyl)-2-methyl-4-hydroxy-2H-1,2-benzothiazine-3-carboxamide 1,1-dioxide, mp 174–177° C. The pure product was further characterized by infrared absorption spectra and elemental analysis.

Anal. Calcd. for $C_{17}H_{20}N_4O_5S$: C, 52.03; H, 5.14; N, 14.28. Found: C, 51.72; H, 5.14; N, 13.93.

EXAMPLE 3

In a 2-liter, three-necked round bottomed reaction flask equipped with magnetic stirrer, dropping funnel (250 ml.) and thermometer, there was placed a filtered solution consisting of 55.0 g. (0.166 mole) of N-(2-pyridyl)-2-methyl-4-hydroxy-2H-1,2-benzothiazine-3-carboxamide 1,1-dioxide dissolved in 660 ml. of methylene chloride. The latter solution, which also contained 0.1 g. of the monoethanolamine salt of N-(2-pyridyl)-2-methyl-4-hydroxy-2H-1,2-benzothiazine-3-carboxamide 1,1-dioxide as seed, was initially prepared by first dissolving the solid material in 610 ml. of methylene chloride contained in an Erlenmeyer flask at 25° C. with the aid of gentle magnetic stirring. The additional 50 ml.-amount of methylene chloride was then used as a wash in transferring the solution to the aforementioned reaction flask. At this point, the latter flask and its contents were heated to 27° C. with the aid of a steam bath and the entire system was subjected to constant and vigorous agitation, while a solution consisting of 10.7 g. (0.175 mole) of ethanolamine dissolved in 110 ml of fresh methylene chloride was slowly added thereto during the course of a 50-minute period. Upon completion of this step, the spent reaction mixture was stirred (i.e., granulated) at 27° C. for a period of one hour and then filtered on a Büchner funnel to afford the crystalline salt. The latter product was dried in a vacuum oven at 35° C. to constant weight and there were obtained in this manner 63.1 g. of the pure monoethanolamine salt of N-(2-pyridyl)-2-methyl-4-hydroxy-2H-1,2-benzothiazine-3-carboxamide 1,1-dioxide, m.p. 171–174° C. The net yield of pure product therefore amounted to 63.0 g. (96.8%). The pure product was further characterized by means of nuclear magnetic resonance spectra and elemental analysis and was identical in every respect with the product of Example 2.

Anal. Calcd. for $C_{17}H_{20}N_4O_5S$: C, 52.03; H, 5.14; N, 14.28. Found: C, 52.09; H, 5.15; N, 14.30.

EXAMPLE 4

To a suspension of 2.0 g. (0.00604 mole) of N-(2-pyridyl)-2-methyl-4-hydroxy-2H-1,2-benzothiazine-3-carboxamide 1,1-dioxide in 300 ml. of water, there was added 687 mg. (0.00634 mole) of diethanolamine and the resulting mixture was warmed on a steam bath for a period of three minutes. The yellow solution so obtained was then filtered to remove a very small amount of white solids, followed by concentration of the resulting filtrate in vacuo to yield a yellow oil as the residual liquid. Treatment of the latter material with 200 ml. of an ethyl acetate/chloroform (3:2 by volume) solvent system, followed by stirring at room temperature ($\sim$25° C.) overnight ($\sim$18 hours) under a dry nitrogen atmosphere then gave a yellow gum which was subsequently recovered by decanting the solvent. The gum was then triturated with 100 ml. of chloroform and warmed on a steam bath for a period of two minutes (just until reflux), followed by sufficient scratching to induce crystallization. The mixture was then allowed to cool to room temperature and thereafter stirred at that point for a period of 2.5 hours while under a dry nitrogen atmosphere. After removing the solid crystalline material via suction filtration and washing same with fresh chloroform solvent, followed by drying in vacuo to constant weight, there was ultimately obtained a 2.11 g. (80%) yield of the pure diethanolamine salt of N-(2-pyridyl)-2-methyl-4-hydroxy-2H-1,2-benzothiazine-3-carboxamide 1,1-dioxide, m.p. 143–146° C. The pure product was further characterized by means of infrared absorption spectra and elemental analysis.

Anal. Calcd. for $C_{19}H_{24}N_4O_6S$: C, 52.28; H, 5.54; N, 12.84. Found: C, 52.04; H, 5.40; N, 12.55.

EXAMPLE 5

A dry solid pharmaceutical composition is prepared by blending the following materials together in the proportions by weight specified below:

| | |
|---|---|
| The ethylenediamine salt of N—(2-pyridyl)-2-methyl-4-hydroxy-2H—1,2-benzothiazine-3-carboxamide 1,1-dioxide | 5.88 |
| Microcrystalline cellulose | 34.00 |
| Corn starch, U.S.P. | 9.08 |
| Magnesium stearate | 1.04 |

After the dried composition is thoroughly blended, tablets are punched from the resulting mixture, each tablet being of such a size that it contains 5 mg. of the active ingredient. Other tablets are also prepared in a similar fashion containing 10, 25 and 50 mg. of the active ingredient, respectively, by merely using the appropriate amount of the tablet blend in each case.

EXAMPLE 6

A dry solid pharmaceutical composition is prepared by combining the following materials together in the proportions by weight indicated below:

| | |
|---|---|
| The monoethanolamine salt of N—(2-pyridyl)-2-methyl-4-hydroxy-2H—1,2-benzothiazine-3-carboxamide 1,1-dioxide | 59.21 |
| Dicalcium phosphate, anhydrous | 230.10 |
| Corn starch, U.S.P. | 32.50 |
| Sodium lauryl sulfate | 0.32 |
| Magnesium stearate | 2.87 |

The dried solid mixture so prepared is then thoroughly agitated so as to obtain a powdered product that is completely uniform in every respect. Hard gelatin (No.2) capsules containing the pharmaceutical composition are then prepared, employing a sufficient quantity of material in each instance so as to provide each capsule with 50 mg. of the active ingredient.

EXAMPLE 7

An aqueous propylene glycol solution containing the diethanolamine salt of N-(2-pyridyl)-2-methyl-4-hydroxy-2H-1,2-benzothiazine-3-carboxamide 1,1-dioxide is prepared by dissolving the latter compound in propylene glycol-water (1:4 by weight) containing 1% by weight of trisodium phosphate and adjusted to an apparent pH of 8.0. The amount of compound employed is such that the resulting solution contains 5 mg. of the active ingredient per each ml. of solution. The solution is then sterilized by means of filtration through a 0.2 μm pore size cellulose membrane. The sterile aqueous propylene glycol solution so obtained is then suitable for intramuscular administration to animals.

EXAMPLE 8

An aqueous injectable solution is prepared by first intimately admixing one part by weight of the monoethanolamine salt of N-(2-pyridyl)-2-methyl-4-hydroxy-2H-1,2-benzothiazine-3-carboxamide 1,1-dioxide with 2.5 parts by weight of disodium phosphate with the aid of a mortar and pestle. The ground dry mixture so obtained is then sterilized with ethylene oxide and thereafter aseptically placed into vials and sealed. For purposes of intravenous administration, a sufficient amount of distilled water is added to each of the filled vials before use so as to ultimately provide a solution which contains 10 mg. of the active ingredient per each ml. of injectable solution.

EXAMPLE 9

A tablet formulation is prepared by blending the following materials together in the proportions by weight specified below:

| | |
|---|---|
| The monoethanolamine salt of N—(2-pyridyl)-2-methyl-4-hydroxy-2H—1,2-benzothiazine-3-carboxamide 1,1-dioxide | 23.92 |
| Microcrystalline cellulose | 311.03 |
| Modified pregelatinized starch, N.F. | 84.00 |
| Magnesium stearate | 0.945 |
| Sodium lauryl sulfate | 0.105 |

After the dried composition is thoroughly blended, tablets are punched from the resulting mixture, each tablet being of such a size that it contains 20 mg. of the active ingredient. Other tablets are also prepared in a similar fashion containing 5, 10 and 50 mg. of the active ingredient, respectively, by merely using the appropriate amount of the tablet blend in each case.

EXAMPLE 10

A tablet formulation is prepared by blending the following materials together in the proportions by weight specified below:

| | |
|---|---|
| The monoethanolamine salt of N—(2-pyridyl)-2-methyl-4-hydroxy-2H—1,2-benzothiazine-3-carboxamide 1,1-dioxide | 23.69 |
| Dicalcium phosphate, anhydrous | 113.37 |
| Polyvinylpyrrolidone | 50.00 |
| Modified pregelatinized starch, N.F. | 10.00 |
| Magnesium stearate | 2.65 |
| Sodium lauryl sulfate | 0.294 |

After the dried composition is thoroughly blended, tablets are punched from the resulting mixture, each tablet being of such a size that it contains 20 mg. of the active ingredient. Other tablets are also prepared in a similar fashion containing 5, 10 and 50 mg. of the active ingredient, respectively, by merely using the appropriate amount of the tablet blend in each case.

What is claimed is:

1. A water-soluble base salt of an acidic, anti-inflammatory 1,2-benzothiazine, said salt being a member selected from the group consisting of the ethylenediamine, monoethanolamine and diethanolamine salts of N-(2-pyridyl)-2-methyl-4-hydroxy-2H-1,2-benzothiazine-3-carboxamide 1,1-dioxide.

2. A compound as claimed in claim 1 which is an ethylenediamine salt.

3. A compound as claimed in claim 1 which is a monoethanolamine salt.

4. A compound as claimed in claim 1 which is a diethanolamine salt.

5. A pharmaceutical composition comprising a pharmaceutically acceptable carrier and an effective anti-arthritic amount of a compound as claimed in claim 1.

6. The composition as claimed in claim 5 wherein the compound is the monoethanolamine salt of N-(2-pyridyl)-2-methyl-4-hydroxy-2H-1,2-benzothiazine-3-carboxamide 1,1-dioxide.

7. A method for treating arthritic conditions in a warm-blooded animal, which comprises administering to said animal an effective anti-arthritic amount of a compound as claimed in claim 1.

8. The method as claimed in claim 7 wherein the compound administered is the monoethanolamine salt of N-(2-pyridyl)-2-methyl-4-hydroxy-2H-1,2-benzothiazine-3-carboxamide 1,1-dioxide.

* * * * *